United States Patent [19]

Chang

[11] 4,169,369
[45] Oct. 2, 1979

[54] METHOD AND THIN FILM SEMICONDUCTOR SENSOR FOR DETECTING $NO_x$

[75] Inventor: Shih-Chia Chang, Troy, Mich.

[73] Assignee: General Motors Corporation, Detroit, Mich.

[21] Appl. No.: 927,488

[22] Filed: Jul. 24, 1978

[51] Int. Cl.$^2$ .......................................... G01N 27/04
[52] U.S. Cl. ...................................................... 73/23
[58] Field of Search ................... 73/23, 27 R; 338/34; 340/634; 23/232 E; 422/88, 98

[56] References Cited

U.S. PATENT DOCUMENTS

| | | | |
|---|---|---|---|
| 3,901,067 | 8/1975 | Boardman et al. | 73/23 |
| 3,955,929 | 5/1976 | Kawakami et al. | 73/27 R |
| 4,030,340 | 6/1977 | Chang | 73/23 |

OTHER PUBLICATIONS

Ichinose et al., "Ceramic Oxide Semiconductor Elements for Detecting Gaseous Components," Ceramics 11, (3), pp. 203-211, 1976.
Seiyama et al., "Study on a Detector for Gaseous Components Using Semiconductive Thin Films," Analytical Chemistry, vol. 38, No. 8, pp. 1069-1073, Jul. 1966.

*Primary Examiner*—Stephen A. Kreitman
*Attorney, Agent, or Firm*—George A. Grove

[57] ABSTRACT

The concentration of $NO_x$ in a gaseous mixture is measured using a solid state sensor comprising a surface thin film of semiconductive material. In a preferred embodiment, the thin film semiconductor comprises tin oxide having an oxygen to tin atomic ratio of between 1.5 and 1.95, preferably between 1.8 and 1.9, and is formed by reactive sputtering from a tin or tin oxide target in an argon-oxygen atmosphere. The electrical resistance of the tin oxide thin film is highly sensitive to $NO_x$ species, but is essentially unaffected by the presence of other common gases such as CO, $H_2$, $O_2$, $SO_2$, $NH_3$ and hydrocarbons. Water vapor present in the mixture has a small effect upon the resistance of the film. The thin film tin oxide sensor may be used to measure $NO_x$ in air and, in one particularly advantageous aspect of this invention, is employed to measure $NO_x$ emissions in automotive exhaust gas.

9 Claims, 5 Drawing Figures

METHOD AND THIN FILM SEMICONDUCTOR SENSOR FOR DETECTING $NO_x$

BACKGROUND OF THE INVENTION

This invention relates to measuring the concentration of nitrogen oxide compounds $NO_x$ in a gaseous mixture using a solid state sensing element comprising a semiconductor thin film. More particularly, this invention relates to determining the $NO_x$ concentration in a gaseous mixture by measuring the resistance of a tin oxide semiconductor thin film exposed to the gas. This invention is particularly useful for measuring $NO_x$ emissions in automotive exhaust gas.

Concern for air pollution has focused in a major part upon the emission of gaseous nitrogen oxide compounds, particularly from automobile internal combustion engines. Because nitrogen assumes a plurality of oxidation states, several nitrogen oxide compounds have been identified. As a group, these compounds are normally gases and are generally referred to by the symbol "$NO_x$", which relates to their common empirical formula. The most sigificant $NO_x$ are nitric oxide NO and nitrogen dioxide $NO_2$. These two compounds are the principle $NO_x$ constituents found in automotive exhaust gas and in gases emitted from power plants and similar industrial sites.

When monitoring gaseous emissions, it is frequently desired to measure the gas composition at the site from which it emanates. Known methods for measuring the $NO_x$ concentration of a gas typically involve carefully controlled reactions or employe delicate and expensive instruments and, therefore, are not easily adapted for on-site measurements. For example, one widely accepted method involves chemiluminescence. Ozone is added to a gaseous sample and reacts with nitric oxide NO therein to produce an excited nitrogen dioxide $NO_2$ molecule that subsequently emits light. Thus, the NO concentration is related to the intensity of the emitted light, which is measured by a photoelectric cell. Since chemiluminesence analysis is specific for NO, sample pretreatment is required to reduce initially present $NO_2$ in order to measure the total $NO_x$ concentration. Because chemiluminescence analysis requires ozone reactant, carefully controlled reaction conditions, sample pretreatment, and delicate instruments, it is generally not suited for on-site $NO_x$ detection. For similar reasons, other known wet chemistry or instrumental methods useful for accurate laboratory $NO_x$ analysis are typically not suitable for measurements in the field.

Particular difficulty has been encountered in attempting to study and monitor $NO_x$ emissions of a moving automobile. Automobile engines operate over a wide range of conditions that are subject to continuous and rapid change. The hot exhaust gases contain varying concentrations of oxidizing species ($NO_x$ and $O_2$) and also reducing species (CO and hydrocarbons). Also, on-board $NO_x$ detection must not significantly interfere with the flow of the exhaust gases. Therefore, what is needed for on-board $NO_x$ detection is a simple, direct method of accurately measuring the total $NO_x$ that provides continuous readings, responds rapidly to changes in the $NO_x$ concentration, and does not require the addition of reagents. The measurements must be made without sample pretreatment and without interference by other exhaust constituents. Any instruments employed must be durable, easily incorporated into the exhaust system, and have a low power consumption so as to be portable. Because no suitable on-board method has heretofore been available, automotive $NO_x$ studies have typically been limited to the dynamometer laboratory.

It has heretofore been known that the resistance of a thin film semiconductor exposed to a gaseous mixture is sensitive to the presence of certain species in the gas. Thus, thin film semiconductors have been used to measure the concentration of gaseous materials. For example, tin oxide thin films have been employed to measure reducing gases, such as hydrogen, hydrogen sulfide or a hydrocarbon, or oxidizing gases, such as oxygen. In view of this, it is totally unexpected that a highly selective tin oxide sensor could be adapted to measure the $NO_x$ concentration in the presence of these and other oxidizing and reducing compounds.

It is an object of this invention to provide a method for detecting $NO_x$ present in a gaseous mixture that does not require the addition of reagents to the mixture and does not employ delicate, expensive instruments. It is a further object of this invention to provide a method for accurately measuring the total $NO_x$ concentration of a gas, which measurement may be made without first treating the gas to change various $NO_x$ species to a single form or to remove other common gaseous constituents. The method of this invention is particularly useful for determining the total $NO_x$ concentration in automotive exhaust gases directly and without significant interference from $O_2$, CO, hydrocarbons or other typical exhaust constituents.

It is a further object of my invention to provide a method for continuously monitoring the $NO_x$ concentration in a gas stream, which method responds quickly to changes in the gas $NO_x$ concentration and does not significantly interfere with the flow of the gas. More particularly, it is an object of my invention to directly and accurately measure the total $NO_x$ concentration in a gas by exposing the gas to a solid state sensor comprising a thin film semiconductor whose resistance is directly related to the presence of $NO_x$.

It is a still further object of this invention to provide a solid state sensor comprising a thin film semiconductor whose resistance is sensitive to the presence of $NO_x$ but relatively insensitive to the presence of other oxidizing and reducing species, most notably $O_2$, $H_2$, CO, and hydrocarbons, whereby the resistance of the semiconductor provides an accurate means for calculating the $NO_x$ concentration. The sensor of this invention is durable, inexpensive and simple to manufacture and may be operated at low electrical power levels so as to be portable. In one aspect of this invention, the sensor is easily incorporated into an automotive exhaust system to provide continuous, on-board measurement of $NO_x$ emissions.

SUMMARY OF THE INVENTION

In a preferred embodiment, these and other objects are accomplished by exposing a solid state sensing element comprising a thin film of semiconductive tin oxide to a gaseous mixture containing nitrogen oxide species. It has been found that the value of the electrical resistance of the tin oxide thin film depends upon the amount of $NO_x$ present and thereby provides a method for determining the $NO_x$ concentration of a gas. The $NO_x$-sensitive tin oxide film of this invention is an N-type semiconductor having a composition intermediate pure stannic oxide $SnO_2$ and pure stannous oxide SnO. More specifically, thin films having an oxygen-to-tin atomic ratio of between 1.5 and 1.95 respond suitably to the presence of $NO_x$, with films having a ratio between 1.8 and 1.9 being extremely sensitive to $NO_x$. Optimum response is obtained when the tin oxide film is heated to a temperature between 150° to 300° C. and preferably to about 250° C. When the resistance of the film is measured, the sensor responds quickly and reproducably to changes in the $NO_x$ concentration, but is essentially unaffected by several other common oxidizing and reducing gaseous compounds.

In a preferred embodiment, the sensing element of this invention is produced by depositing a tin oxide layer upon an inert electrically insulating substrate. Preferably, the film is deposited by reactive RF sputtering from a metallic tin target in an argon-oxygen atmosphere. Film thicknesses of 600 to 10,000A° are suitable, with film thicknesses of about 1,000A° preferred. The film is then heated in air to an elevated temperature preferably between 350° to 450° C. Heat treatment of a thin film deposited by reactive RF sputtering stabilizes the film and optimizes its sensitivity to the presence of $NO_x$.

When the tin oxide thin film is heated to the desired operating temperature and brought in contact with a gaseous sample, the logarithm of the resistance across the film increases in direct proportion to the logarithm of the concentration of $NO_x$ in the sample. Thus, the $NO_x$ concentration of an unknown sample can be determined by conventional analytical chemistry methods, for example, by reference to a graph prepared using known gaseous mixtures. The film resistance is easily measured using spaced electrodes and a conventional ohmmeter. While not limited to any particular theory, it is believed that sensor operation is based upon a chemisorption phenomenon. That is, $NO_x$ species are absorbed into the tin oxide semiconductor thin film. The absorbed molecules, interact with crystal defects near the surface of the semiconductor film. The interaction alters the film's electrical properties and particularly its resistance. The amount of gas absorbed and thus the effect upon the film's resistance depends upon the concentration of $NO_x$ in the ambient gas.

Although it is believed that the thin film semiconductor sensor of this invention is responsive to any nitrogen oxide compound, it is particularly useful for detecting nitric oxide NO and nitrogen dioxide $NO_2$. Thus, the sensor affords a method for determining the total concentration of all $NO_x$ species present in a gaseous mixture without first treating the sample to reduce the various species to a single compound. The thin film semiconductor responds accurately to $No_x$ concentrations in excess of 500 ppm and is particularly advantageously employed to accurately measure small $NO_x$ concentration of less than 50 ppm. The thin tin oxide film is highly selective for $NO_x$ and may be used to measure small concentrations of $NO_x$ even in air. This is surprising in view of the oxygen in air which would be expected to interfere the measurement of another oxidizing species, such as $NO_x$. The film is negligibly affected by the presence of common reducing gases such as carbon monoxide, methane, propylene, hydrogen and ammonia. Although the sensor responds somewhat to water vapor present in the gas, this response is small in comparison to its $NO_x$ sensitivity and is easily compensated for.

Thus, this invention provides a method for measuring the total $NO_x$ concentration of a gaseous sample directly and without the addition of reagents. Resistance readings may be continuously made and respond relatively quickly to changes in the $NO_x$ concentration. In marked contrast to typically laboratory $NO_x$ analysis procedures, this method employs a small, easily manufactured sensing element of rugged construction. The sensor requires low operating electrical power, thereby rendering it portable. Thus, the method of this invention is useful for on-site monitoring of the $NO_x$ concentration of a gaseous stream. In one aspect of this invention, the sensor is incorporated into an automotive exhaust system for on-board monitoring of exhaust emissions.

DETAILED DESCRIPTION OF THE INVENTION

Figure 1:
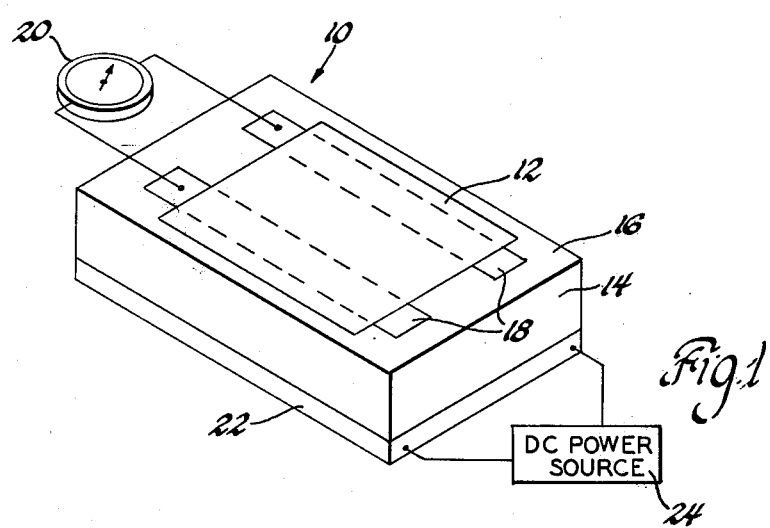
FIG. 1 is a perspective view of the solid state semiconductor sensor of this invention.

Referring to FIG. 1, a sensing element 10 comprising a thin film semiconductor 12 is illustrated for measuring the $NO_x$ concentration of a gaseous mixture in accordance with a preferred embodiment of this invention. Sensor 10 comprises an alumina body 14 having dimensions of approximately 5 mm.×5 mm.×0.5 mm. Alumina is preferred because it is a good electrical insulator, but has adequate thermal conduction to permit uniform heating of sensor 10. Body 14 has a first major surface 16 having a surface finish (as measured perpendicular to the surface between peaks and valleys) of approximately 380A°. It is believed that the roughness of surface 16 creates defects in a thin film applied to that surface, which defects subsequently become active sites for $NO_x$ sensing.

Two opposite, parallel gold-glass electrodes 18 having dimensions of 1 mm.×2 mm. are applied to surface 16 using silk screen technology and fired. Electrodes 18 are spaced apart by a distance of approximately 1.5 mm. During sensor operation, electrodes 18 were connected to ohmmeter 20 having low power and a substantially constant current to measure the resistance of film 12. Maintaining sensor 10 at a constant temperature is critical to making the most accurate measurements. Since a current passing through a resisting material generates heat, the use of a low, constant current is preferred to avoid variation in the heat generated. In this embodiment, the resistance was measured using a constant current of one microampere.

A resistance heater 22 was applied to the entire surface of body 14 opposite surface 16. The heater material displayed relatively constant and temperature independent resistance over the range of 150°–300° C. Adjacent corners of heater 22 were connected to a conventional DC power source 24. In this embodiment, it was found that that heater 22 had a resistance of about 50 ohms and that approximately one watt was necessary to heat sensor 10 to its operating temperature. A chromel constantan thermocouple (not shown) was attached to the middle of the heater surface and provided a suitable signal for electrically controlling power source 24 and thereby maintaining sensor 10 at a substantially constant temperature.

The tin oxide, $NO_x$-sensitive film 12 of this invention was applied to surface 16 of body 14 over electrodes 18. Since the resistance is measured for that portion of the film between the electrodes, it is essential that film 12 be continuous over that area. Film 12 was deposited by reactive RF sputtering from a tin target in a low pressure oxygen-argon atmosphere. A conventional mask was used to expose only that portion of surface 16 where desposition was desired. Within a conventional RF discharge plasma apparatus, substrate 14 was positioned on one electrode such that surface 16 faced a metallic tin target positioned upon the second electrode. The substrate-target distance was about 7.6 cm. The atmosphere contained approximately 6 millitorr partial pressure argon and approximately 4 millitorr partial pressure oxygen. The RF plasma was generated with a forward power of 400 watts and an accelerating voltage of 2.2 kilovolts (the target being cathodic). During sputtering, the temperature of substrate 14 did not exceed 200° C. Under these conditions, a suitable tin oxide film was deposited after about five minutes.

The deposited tin oxide film was then stabilized by heating it in air at a temperature between 350°–450° C. for two hours. Stabilization in this fashion was found to be extremely important to optimizing the film's $NO_x$ sensitivity.

The tin oxide film 12 produced by the aforementioned reactive RF sputtering and heat stabilization was approximately 1000A° thick. Using both Auger Electron Spectroscopy (AES) and Electron Spectroscopy for Chemical Analysis (ESCA), the oxygen to tin atomic ratio of the film was determined to be $1.85 \pm 0.05$ and to be substantially uniform across the film thickness. Analysis also indicated that the film was substantially free of contaminates except for trace amounts of carbon near the surface. Transmission election diffraction revealed a polycrystalline film structure.

Figure 2:
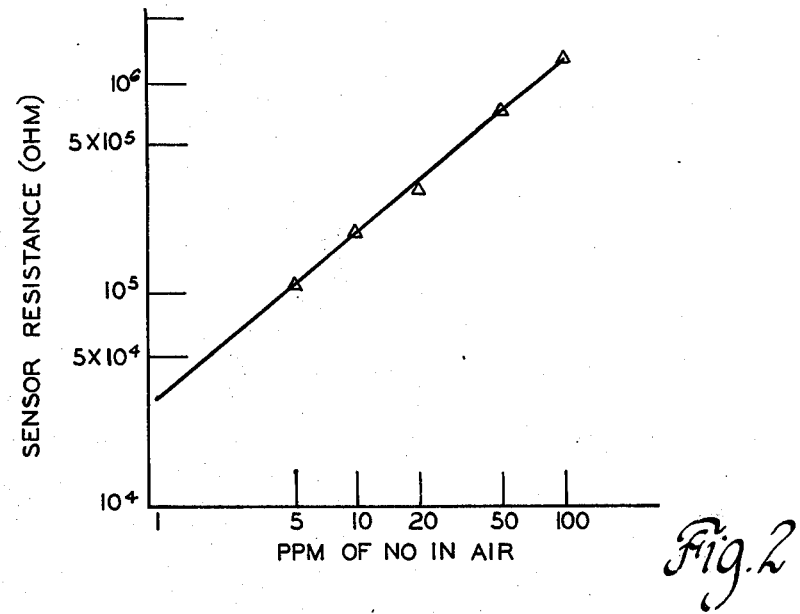
FIG. 2 is a graph of the electrical resistance of a tin oxide thin film as a function of the concentration of nitric oxide NO in air.

$NO_x$ measurements were made by heating sensor 10 to a temperature of about 250° C. using resistance heater 22 and measuring the resistance of the tin oxide thin film 12 using electrodes 18 and ohmmeter 20. The sensor was tested by exposing it to a gaseous sample contained in an airtight container. The samples consisted of room temperature air and a controlled amount of nitric oxide NO. FIG. 2 illustrates the film resistance as a function of the NO concentration, plotted on log-log coordinates. The film resistance in a blank air sample (no NO added) was about $1 \times 10^4$ ohm. FIG. 2 shows that the logarithm of the sensor resistance increases linearly with the logarithm of the NO concentration. Further experiments have demonstrated that this linear relationship continues for greater NO concentration up to at least 500 ppm. In these experiments wherein the sample was prepared and then the sensor introduced into the container, response time was typically about 15 seconds and the recovery time, the time after the container was vented until the thin film sensor returned to its air resistance, was typically 30 seconds.

Figure 3:
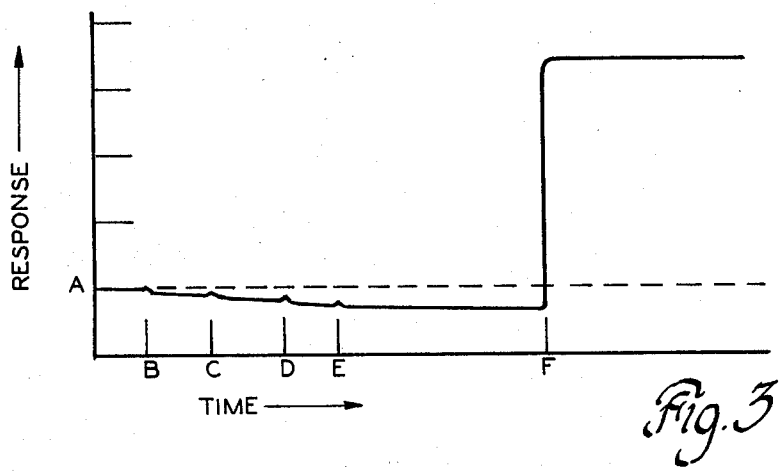
FIG. 3 is a graph showing the response of a thin film semiconductor sensor of this invention to changes in the sample composition.

The sensitivity of the thin film semiconductor sensor was determined for several other common oxidizing and reducing gases. The results of one typical test are presented in FIG. 3, wherein the abscissa represents time and the ordinate is a non-linear scale showing the sensor response in terms of its increased electrical resistance. The response of the sensor exposed to air in a sealed box container is represented by the base line A. A predetermined amount of carbon monoxide CO to produce a 300 ppm mixture was introduced into the box at time B. A slight decrease in the film resistance is shown. At time C, hydrogen $H_2$ to a concentration of 300 ppm was added to the CO and air mixture. Again, the sensor resistance decreased slightly. At time D, a calculated amount corresponding to 300 ppm propylene $C_3H_6$ was introduced into the $H_2$—CO-air mixture. The sensor again showed a slight decrease in resistance. At time E, 300 ppm methane $CH_4$ was added to the mixture and had a negligible affect upon the sensor resistance. The responses to 300 ppm concentrations of CO, $H_2$, $C_3H_6$ and $CH_4$ are in striking contrast to the dramatic increase in resistance at time F when a small amount of nitric oxide NO corresponding to 20 ppm was introduced into the sample. Thus, FIG. 3 shows that the thin film semiconductor sensor of this invention responds quickly and is highly sensitive to $NO_x$, but is essentially unaffected by the presence of large quantities of common reducing gases. In other experiments, it was found that the film response to 50 ppm NO in air was disturbed by less than 1% by the presence of 50 ppm $H_2$, 50 ppm CO and 50 ppm $C_3H_6$. Other tests have demonstrated that the sensor is similarly unaffected by the presence of sulphur dioxide or ammonia. It has also been found that, for measurements made in air and in other gases containing significant amounts of oxygen (e.g., automotive exhaust gases containing about 5% oxygen), substantial variations in the oxygen concentration do not affect the sensor response.

Figure 4:
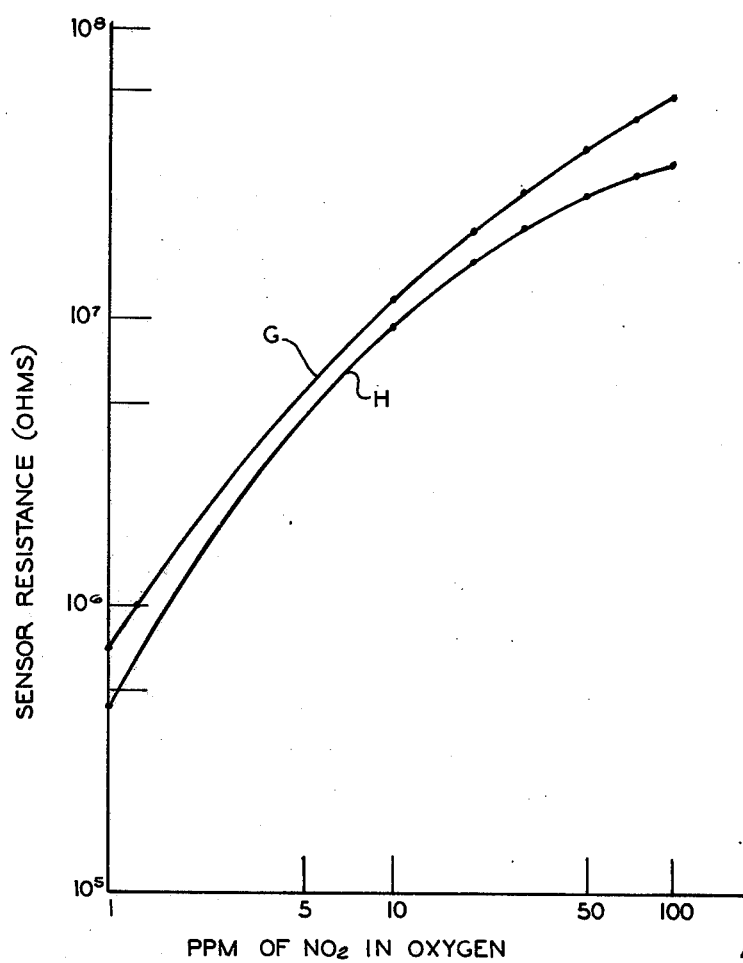
FIG. 4 is a graph showing the response of a thin film semiconductor sensor as a function of the concentration of nitrogen dioxide in oxygen.

Water vapor has a small, but significant effect upon the tin oxide film resistance. This effect is shown in FIG. 4, wherein the sensor response in ohms is plotted on log-log coordinates against the nitrogen dioxide $NO_2$ concentration in ppm. Curve G represents the response to $NO_2$ in dry room temperature oxygen. Curve H shows a similar response to $NO_2$ in room temperature oxygen gas saturated with water vapor. It is seen that the effect of extreme variations (dry to saturated) in the sample water concentration is relatively minor in comparison to the sensitivity of the sensor for $NO_2$. Also, at low $NO_2$ concentrations, the difference in sensor response due to $NO_x$ is substantially the same for samples wherein the amount of water is constant. Thus, the sensor can provide accurate readings even in the presence of water. It is well within the skill of the art to dry a sample and therefore compensate for any water present. However, it is believed that only in the most sensitive of analysis is this compensation necessary.

FIG. 4 also shows that the tin oxide thin film sensor responds to nitrogen dioxide as well as nitric oxide, as shown in FIG. 2. Different sensors were used to prepare FIGS. 2 and 4. These sensors differed primarily in the size and thickness of the tin oxide film and slightly in their oxygen to tin ratios. Because of the differences, the absolute resistance of these films exposed to the same gas (such as a blank or standard mixture) varies. Although direct comparisons of FIGS. 2 and 4 cannot be accurately made, it has been found that the resistance change per ppm $NO_2$ is generally greater than per ppm NO, typically by a factor of about 5. Because the thin film tin oxide sensor responds to both NO and $NO_2$, it is useful for estimating the total $NO_x$ concentration and may provide reasonably accurate measurements of the total $NO_x$ in samples wherein the NO to $NO_2$ ratio is constant.

Figure 5:
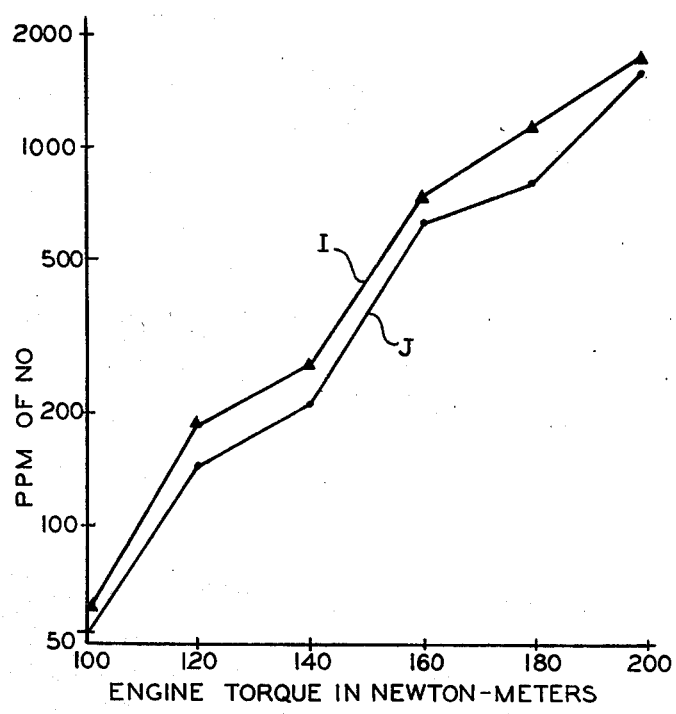
FIG. 5 is a graph showing the automotive exhaust $NO_x$ emissions as a function of engine operation as measured by the sensor of this invention and by conventional means.

It has been shown that the sensor of this invention is virtually unaffected by the presence of oxygen, carbon monoxide or hydrocarbons. Therefore, it is particularly useful for measuring the $NO_x$ concentration of automotive exhaust gas. The results of a typical automotive emission analysis conducted in a dynamometer laboratory are presented in FIG. 5. Automotive exhaust gas directly from the engine (no catalytic converter employed) was mixed with nitrogen and exposed to the sensor. The nitrogen-to-exhaust ratio was 40:1 by volume, which reduced the measured $NO_x$ concentration to less than 100 ppm, thereby placing it within a range suitable for accurate detection using the thin film semiconductor sensor. The temperature of the nitrogen-exhaust gas mixture was unknown, but approximately room temperature. The mixture temperature is not considered significant, since the sensor was operated at 270° C. In this experiment, the gas flow past the sensor was about 1000 cc/min. Curve I of FIG. 5 shows the $NO_x$ emissions plotted as ppm of NO on a logarithmic scale, as a function of the engine torque in Newton-meters. Curve J shows measurements made in the same test with a conventional chemiluminescence analyzer. Since the gas was not pretreated to reduce $NO_2$ to NO, the chemiluminescence analyzer measured only the NO concentration and not the $NO_2$ concentration. In contrast, the thin film semiconductor sensor of this invention responds to both NO and $NO_2$, although somewhat more vigorously to the latter. Since the $NO_2$ content in exhaust gas varies up to 20% of the total $NO_x$, this difference accounts for much of the difference in these curves.

In summary, this invention enables the total concentration of $NO_x$ to be accurately measured for a gaseous sample using a solid state sensor having a tin oxide thin surface film of specific tin to oxygen atomic proportions. The sensor is of simple, durable construction and is operated at low power levels. Measurements are made without initial gas treatment and without adding reagents. The sensor is, therefore, suitably adapted for use in the field, i.e., for on-site $NO_x$ measurements. It provides a continuous reading of the $NO_x$ concentration and responds quickly to changes therein. Measurements are negligibly affected by relatively large concentrations of carbon monoxide, methane, propylene, sulphur dioxide, ammonia and other common gases. The sensor is so $NO_x$ sensitive that accurate measurements can be made even in the presence of large and varying concentrations of oxygen, such as in air. Although water does affect the readings, it is small in comparison to the thin film's $NO_x$ sensitivity. The high sensitivity of the tin oxide thin film to $NO_x$ makes the sensor of this invention particularly useful for measuring $NO_x$ emissions in automotive exhaust gases.

Thin films having oxygen to tin atomic ratios of between 1.5 and 1.95 are suitably responsive to $NO_x$. Optimum $NO_x$ sensitivity has been found for films having ratios between 1.8 and 1.9. While the film preferably contains only tin and oxygen, it is recognized that inert material, such as carbon in the preferred embodiment, or a suitable dopant may be present without inhibiting the $NO_x$ sensitivity of the film.

In the preferred embodiment, the tin oxide film thickness was 1000A° and the substrate surface finish was 400A°. It is believed that the roughness of the substrate surface produces defects in the film that become active $NO_x$-sensing sites. Thus, the film thickness and the surface finish are interrelated parameters. If the film is too thin or the surface finish is too rough, the film will be discontinuous. If the substrate surface is too smooth, the film will not have the necessary lattice defects. If the film is too thick, the $NO_x$-defect interactions, which occur near the film surface, will not have a measurable effect upon the overall film resistance. In general, substrates having surface finishes ranging between 300 to 4000A° are suitable for use with tin oxide film ranging between 600 and 10,000A°.

The $NO_x$-sensitive tin oxide thin film is preferably deposited upon the substrate by reactive sputtering from a tin target in an argon-oxygen atmosphere. Although other reactive sputtering techniques may be employed, reactive RF sputtering is preferred because it provides better control over the film deposition. The particular sputtering conditions can be varied from those in the preferred embodiment and acceptable films still deposited. $NO_x$-sensitive films having the desired oxygen to tin ratios have also been deposited by reactive RF sputtering using a $SnO_2$ target in an argon-oxygen atmosphere, wherein the ratio of the partial pressures of argon to oxygen is preferably 7 to 3. Films having similar characteristics can also be produced by vapor deposition followed by oxidation or by the application of a suitable slurry followed by evaporation.

For a film deposited by reactive sputtering, optimum $NO_x$ sensitivity was achieved by heating the sensor in air prior to its use. This heat treatment stabilizes the film's oxygen content and also its resistance. Suitable film stabilization is afforded by heating the sensor to a temperature between 100 and 600° C., preferably between 350° to 450° C.

Materials other than those mentioned above may be used to manufacture the substrate and the electrodes without significantly affecting the performance of the tin oxide thin film. For example, other inert, refractory materials such as steatite, are good electrical insulators and form suitable sensor bodies. Any good electrical conductor may be used for the electrodes. The heater need not be attached to the sensor. Attaching the heater as in the preferred embodiment has the advantage that the sensor can be maintained at a desired temperature without heating the entire sample. For the preferred tin oxide thin film deposited by reactive sputtering, it has generally been found the most accurate readings are obtained by operating the sensor between 150°-300° C. Operated above that temperature range, the sensor responds faster, but typically overshoots. When the sensor is operated below that range, a slow response is obtained that typically represents too low a concentration.

Although this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A method for detecting the presence of $NO_x$ species contained in a gaseous mixture comprising measuring the electrical resistance of a thin film semiconductor exposed to said mixture, said thin film semiconductor comprising polycrystalline tin oxide having an oxygen to tin atomic ratio between 1.5 and 1.95, said film having a known resistance to $NO_x$ free gas environment, a substantial increase in film resistance over said known value indicating the presence of $NO_x$ in the mixture.

2. A method of analyzing a gaseous mixture for the concentration of $NO_x$ species comprising
contacting said gaseous mixture with a thin film comprising polycrystalline tin oxide having an oxygen to tin atomic ratio between 1.5 and 1.95,
maintaining the temperature of the film between 150° and 300° C., and
measuring the electrical resistance of said thin film while exposed to said gaseous mixture, whereby the resistance measurement provides a measure of the $NO_x$ concentration of the gaseous mixture.

3. A method of measuring the concentration of $NO_x$ species contained in a gaseous mixture comprising
contacting said gaseous mixture with a thin film comprising polycrystalline tin oxide having an oxygen to tin atomic ratio between 1.8 and 1.9,
maintaining the temperature of the detecting element between 150° and 300° C., and
measuring the electrical resistance of said thin film while exposed to said gaseous mixture, whereby the resistance measurement provides a measure of the $NO_x$ concentration of the gaseous mixture.

4. A method of measuring the concentration of $NO_x$ species contained in a gaseous mixture, said $NO_x$ species comprising at least one compound selected from the group consisting of NO and $NO_2$, said method comprising measuring the electrical resistance of a semiconductor thin film exposed to said mixture and maintained at a temperature between 150° and 300° C., said semiconductor thin film consisting essentially of a polycrystalline tin oxide material having an oxygen to tin atomic ratio of between 1.5 and 1.95 and being further characterized as being formed by reactive sputtering in a low pressure atmosphere comprising argon and oxygen using a target selected from the group consisting of tin and oxides of tin, the electrical resistance of said film being a measure of the concentration of $NO_x$ in the mixture.

5. A method of measuring the concentration of $NO_x$ species contained in a gaseous mixture, said $NO_x$ species being selected from the group consisting of NO and $NO_2$, said method comprising measuring the electrical resistance of a semiconductor thin film exposed to said mixture and maintained at a temperature between 150° and 300° C., said semiconductor thin film consisting essentially of a polycrystalline tin oxide material having an oxygen to tin atomic ratio of between 1.8 and 1.9 and formed by reactive sputtering in a low pressure atmosphere comprising argon and oxygen using a target selected from the group consisting of tin and oxides of tin, the electrical resistance of said film being a measure of the concentration of $NO_x$ in the mixture.

6. A device for detecting the presence of $NO_x$ species contained in a gaseous mixture, said device comprising
an electrically insulating substrate,
a $NO_x$-sensitive thin film on a surface of said substrate, said film comprising polycrystalline tin oxide semiconductor having an oxygen to tin atomic ratio between 1.5 and 1.95,
heating means for maintaining the film-substrate assembly at a temperature of between 150° and 300° C., and
means for measuring the electrical resistance of the $NO_x$-sensitive thin film, the resistance being a measure of the concentration of $NO_x$ in the gas mixture.

7. A device for detecting the presence of $NO_x$ species contained in a gaseous mixture, said device comprising
an electrically insulating substrate,
a $NO_x$-sensitive thin film on a surface of said substrate, said film comprising polycrystalline tin oxide semiconductor having an oxygen to tin atomic ratio between 1.8 and 1.9,
heating means for maintaining the film-substrate assembly at a temperature of between 150° and 300° C., and
means for measuring the electrical resistance of the $NO_x$-sensitive thin film, the resistance being a measure of the concentration of $NO_x$ in the gas mixture.

8. A device for measuring the concentration of $NO_x$ species contained in a gaseous mixture, said device comprising
an electrically insulating substrate,
a $NO_x$-sensitive thin film on a surface of said substrate, said film consisting essentially of polycrystalline tin oxide having an oxygen to tin atomic ratio between 1.5 and 1.95, said film being further characterized as having been deposited by reactive sputtering in an atmosphere containing argon and oxygen from a target selected from the group consisting of tin and oxides of tin,
heating means for maintaining the film-substrate assembly at a temperature of between 150° and 300° C., and
means for measuring the resistance of the $NO_x$-sensitive thin film, the resistance being a measure of the concentration of $NO_x$ in the gas mixture.

9. A device for measuring the concentration of $NO_x$ species contained in a gaseous mixture, said device comprising
an electrically insulating substrate,
a $NO_x$-sensitive thin film on the surface of said substrate, said film consisting essentially of polycrystalline tin oxide semiconductor having an oxygen to tin atomic ratio between 1.8 and 1.9, said film being further characterized as having been deposited by reactive sputtering in an atmosphere containing argon and oxygen from a target selected from the group consisting of tin and oxides of tin,
heating means for maintaining the film-substrate assembly at a temperature of between 150° and 300° C., and
means for measuring the resistance of the $NO_x$ sensitive thin film, the resistance being a measure of the concentration of $NO_x$ in the gas mixture.

* * * * *